United States Patent
Taggart et al.

(10) Patent No.: US 9,214,094 B2
(45) Date of Patent: Dec. 15, 2015

(54) METHODS AND APPARATUSES FOR EMERGENCY NOTIFICATIONS TO THE HEARING IMPAIRED

(71) Applicant: Sorenson Communications, Inc., Salt Lake City, UT (US)

(72) Inventors: Steve Taggart, Salt Lake City, UT (US); Bruce Johnson, South Jordan, UT (US); Steve Saunders, Kaysville, UT (US); Jarod Cranor, Bountiful, UT (US); Don Brenner, Draper, UT (US); Brian Chevrier, Highland, UT (US); Jennifer Mitchell, Lehi, UT (US)

(73) Assignee: Sorenson Communications, Inc., Salt Lake City, UT (US)

( * ) Notice: Subject to any disclaimer, the term of this patent is extended or adjusted under 35 U.S.C. 154(b) by 235 days.

(21) Appl. No.: 13/838,487

(22) Filed: Mar. 15, 2013

(65) Prior Publication Data
US 2014/0266572 A1    Sep. 18, 2014

(51) Int. Cl.
| | |
|---|---|
| G09B 21/00 | (2006.01) |
| G08B 1/08 | (2006.01) |
| G08B 23/00 | (2006.01) |
| H04Q 1/30 | (2006.01) |
| G10L 25/00 | (2013.01) |
| H04M 11/00 | (2006.01) |
| A61B 5/00 | (2006.01) |
| A61B 5/11 | (2006.01) |

(52) U.S. Cl.
CPC ............ *G09B 21/009* (2013.01); *A61B 5/0022* (2013.01); *A61B 5/1128* (2013.01); *A61B 2505/01* (2013.01)

(58) Field of Classification Search
CPC ............ G08B 23/00; G08B 1/08; G08B 6/00; G08B 5/224; A45B 3/00; A61B 5/0031; A61B 5/0002; G09B 21/009; H04M 3/42391
USPC ............ 340/4.1, 4.13, 539.12, 501, 7.6, 7.61; 704/271; 379/52
See application file for complete search history.

(56) References Cited

U.S. PATENT DOCUMENTS

| | | | | |
|---|---|---|---|---|
| 7,277,858 B1 * | 10/2007 | Weaver | ............... | G09B 21/009 379/52 |
| 7,671,732 B1 * | 3/2010 | Sennett | ............... | G08B 6/00 340/539.11 |
| 8,253,527 B2 * | 8/2012 | Yang | ............... | G08B 13/19613 340/4.1 |
| 2004/0254868 A1 * | 12/2004 | Kirkland | ............... | H04W 4/023 705/35 |
| 2005/0129185 A1 * | 6/2005 | McClelland | ...... | H04M 3/42391 379/52 |
| 2011/0095881 A1 * | 4/2011 | Rosentel | ............... | G08B 27/008 340/501 |

* cited by examiner

*Primary Examiner* — George Bugg
*Assistant Examiner* — Munear Akki
(74) *Attorney, Agent, or Firm* — TraskBritt

(57) ABSTRACT

Systems and methods for communicating emergency alerts to a hearing-impaired user are disclosed. Queries are performed to one or more emergency alert databases to develop emergency alert notifications. At least some of the emergency alert notifications are filtered responsive to user selected criteria to select one or more filtered emergency alerts. An attention desired indicator is transmitted to a hearing-impaired user device that subscribes to a hearing-impaired relay service supported by the server if the one or more filtered emergency alerts are present. The filtered emergency alerts are transmitted to the hearing-impaired user device in response to a emergency information query from that user device.

18 Claims, 7 Drawing Sheets

| Emergency Alert |
|---|
| Red Flag Warning issued October 25 at 4:34AM EDT expiring October 25 at 7:00PM EDT by NWS Tallahassee http://www.srh.noaa.gov/tlh/ |
| ...RED FLAG WARNING IN EFFECT FOR THE SOUTHEAST FLORIDA BIG BEND FROM 2 PM UNTIL 7 PM EDT TODAY DUE TO LONG DURATIONS OF RELATIVE HUMIDITY VALUES LESS THAN 35 PERCENT COINCIDENT WITH DISPERSION INDICES ABOVE 75... .A RIDGE OF HIGH PRESSURE WILL SLOWLY SLIDE TO THE NORTH OF THE FORECAST AREA DURING THE NEXT COUPLE OF DAYS. EXPECT ONE MORE DAY  Expected<br><br>Expected<br><br>Severe |

*FIG. 7*

METHODS AND APPARATUSES FOR EMERGENCY NOTIFICATIONS TO THE HEARING IMPAIRED

FIELD

Embodiments of the present disclosure relate to systems and methods for hearing impaired communications and, more particularly, to systems and methods for presenting emergency warnings to the hearing impaired.

BACKGROUND

Emergency broadcast technologies exist for notifying people about emergencies through radio and television broadcasts. Existing broadcast technologies, such as Cell Broadcast, Multimedia Broadcast/Multicast Services, and video broadcasts, have been proposed to support emergency alert notification(s) to wireless subscribers. A problem with such broadcast technologies is that the end user does not know when an emergency alert is being broadcast, and thus does not know that he or she needs to tune to an appropriate broadcast channel for the emergency alert information. This situation can be exacerbated if the end user has a disability, such as a hearing impairment.

Conventionally, communication systems for the hearing impaired include a variety of communication devices and services. By way of example, Sorenson Communications® offers the Ntouch® VP videophone and the VP-200 videophone that utilize the Sorenson Video Relay Service,® a service that provides sign language interpretation to hearing impaired video phone users.

There is a need for methods and apparatuses to emergency notifications to the hearing impaired.

BRIEF SUMMARY

Embodiments of the present disclosure include a server for providing emergency alerts to a hearing-impaired user. The server includes a memory configured for storing computing instructions and a processor operably coupled to the memory and configured for executing the computing instructions. The computing instruction cause the processor to query one or more emergency alert databases to develop emergency alert notifications and filter at least some of the emergency alert notifications responsive to user selected criteria to select one or more filtered emergency alerts. The computing instruction also cause the processor to transmit an attention desired indicator to a hearing-impaired user device that subscribes to a hearing-impaired relay service supported by the server if the one or more filtered emergency alerts are present and transmit the filtered emergency alerts to the hearing-impaired user device in response to a emergency information query from that user device.

Embodiments of the present disclosure also include a method for communicating emergency alerts to a hearing-impaired user. The method includes performing queries to one or more emergency alert databases to develop emergency alert notifications and filtering at least some of the emergency alert notifications responsive to user selected criteria to select one or more filtered emergency alerts. The method also includes transmitting an attention desired indicator to a hearing-impaired user device that subscribes to a hearing-impaired relay service supported by the server if the one or more filtered emergency alerts are present and transmitting the filtered emergency alerts to the hearing-impaired user device in response to a emergency information query from that user device.

Embodiments of the present disclosure also include a computing device for use by a hearing-impaired user. The computing device includes a display for presenting information to a hearing-impaired user, a memory configured for storing computing instructions, and a processor operably coupled to the memory and configured for executing the computing instructions. The computing instruction cause the processor to send an attention items query to a hearing-impaired relay service that the computing device is associated with requesting to be notified if there are any items that the computing device should consider and send an emergency information query to the hearing-impaired relay service in response to receiving a notification from the hearing-impaired relay service that there are emergency alerts for the computing device to consider. The computing instruction also cause the processor to present information related to the emergency alerts on the display.

BRIEF DESCRIPTION OF THE DRAWINGS

FIG. 7 illustrates an example of an emergency alert delivered to a hearing-impaired user device.

DETAILED DESCRIPTION

Figure 1:
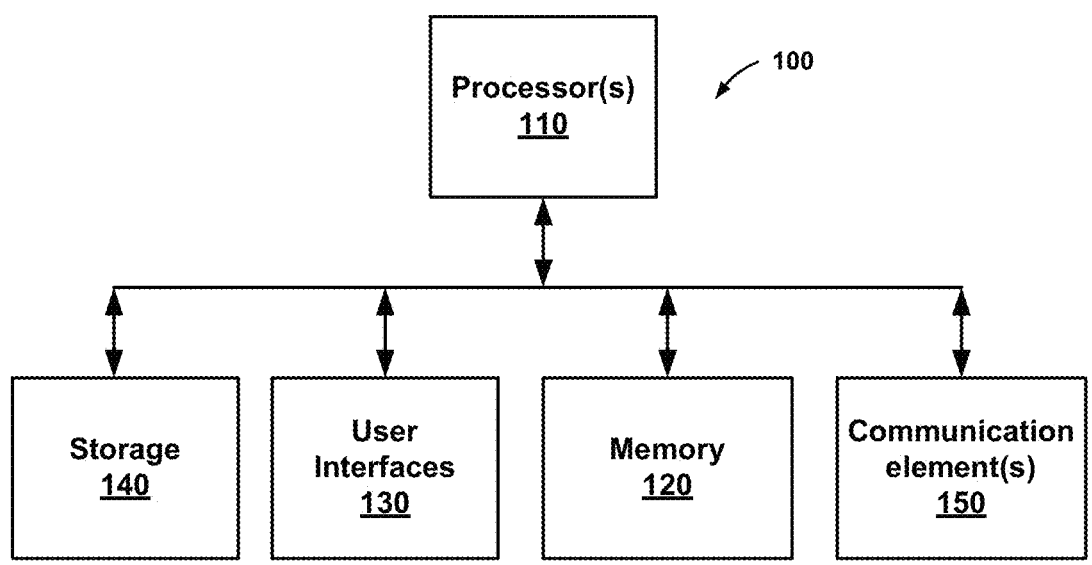
FIG. 1 illustrates a computing system 100 for practicing embodiments of the present disclosure.

In the following detailed description, reference is made to the accompanying drawings which form a part hereof, and in which is shown by way of illustration, specific embodiments in which the present disclosure may be practiced. These embodiments are described in sufficient detail to enable those of ordinary skill in the art to practice the present disclosure. It should be understood, however, that the detailed description and the specific examples, while indicating examples of embodiments of the present disclosure, are given by way of illustration only and not by way of limitation. From this disclosure, various substitutions, modifications, additions rearrangements, or combinations thereof within the scope of the present disclosure may be made and will become apparent to those of ordinary skill in the art.

In accordance with common practice the various features illustrated in the drawings may not be drawn to scale. The illustrations presented herein are not meant to be actual views of any particular method, device, or system, but are merely idealized representations that are employed to describe various embodiments of the present disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

Elements described herein may include multiple instances of the same element. These elements may be generically indicated by a numerical designator (e.g. 110) and specifically indicated by the numerical indicator followed by an alphabetic designator (e.g., 110A) or a numeric indicator preceded by a "dash" (e.g., 110-1). For ease of following the description, for the most part, element number indicators begin with the number of the drawing on which the elements are introduced or most fully discussed. Thus, for example, element identifiers on a FIG. 1 will be mostly in the numerical format 1xx and elements on a FIG. 4 will be mostly in the numerical format 4xx.

As used herein, the terms "connect," "connecting," "connection," and other derivations of "connect" refer to communicating or establishing a communication between two or more elements. These terms do not necessarily mean that there is a physical connection between the elements. The "connection" may be through an appropriate wireless communication network as well as a wired communication network.

FIG. 1 illustrates a computing system 100 for practicing embodiments of the present disclosure. Computer, computing system, communication device, and server may be used interchangeably herein to indicate a system for practicing some embodiments of the present disclosure. The computing system 100 is configured for executing software programs containing computing instructions and may include one or more processors 110, memory 120, one or more communication elements 150, user interface elements 130, and storage 140.

As non-limiting examples, the computing system 100 may be a user-type computer, a file server, a compute server, a notebook computer, a tablet, a handheld device, a mobile device, or other similar computer system for executing software.

The one or more processors 110 may be configured for executing a wide variety of operating systems and applications including the computing instructions for carrying out embodiments of the present disclosure.

The memory 120 may be used to hold computing instructions, data, and other information for performing a wide variety of tasks including performing embodiments of the present disclosure. By way of example, and not limitation, the memory 120 may include Synchronous Random Access Memory (SRAM), Dynamic RAM (DRAM), Read-Only Memory (ROM), Flash memory, and the like.

Information related to the computing system 100 may be presented to, and received from, a user with one or more user interface elements. As non-limiting examples, the user interface elements may include elements such as displays, keyboards, mice, joysticks, haptic devices, microphones, speakers, cameras, and touchscreens. A display on the computing system may be configured to present a graphical user interface (GUI) with information about some embodiments of the present disclosure, as is explained below.

The communication elements 150 may be configured for communicating with other devices or communication networks. As non-limiting examples, the communication elements 150 may include elements for communicating on wired and wireless communication media, such as for example, serial ports, parallel ports, Ethernet connections, universal serial bus (USB) connections IEEE 1394 ("firewire") connections, Bluetooth wireless connections, 802.1 a/b/g/n type wireless connections, and other suitable communication interfaces and protocols.

The storage 140 may be used for storing relatively large amounts of non-volatile information for use in the computing system 100 and may be configured as one or more storage devices. By way of example, and not limitation, these storage devices may include computer-readable media (CRM). This CRM may include, but is not limited to, magnetic and optical storage devices such as disk drives, magnetic tapes, CDs (compact disks), DVDs (digital versatile discs or digital video discs), and other equivalent storage devices.

Software processes illustrated herein are intended to illustrate representative processes that may be performed by the systems illustrated herein. Unless specified otherwise, the order in which the process acts are described is not intended to be construed as a limitation, and acts described as occurring sequentially may occur in a different sequence, or in one or more parallel process streams. It will be appreciated by those of ordinary skill in the art that many steps and processes may occur in addition to those outlined in flow charts. Furthermore, the processes may be implemented in any suitable hardware, software, firmware, or combinations thereof.

When executed as firmware or software, the instructions for performing the processes may be stored on a computer-readable medium. A computer-readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory.

By way of non-limiting example, computing instructions for performing the processes may be stored on the storage 140, transferred to the memory 120 for execution, and executed by the processors 110. The processors 110, when executing computing instructions configured for performing the processes, constitutes structure for performing the processes and can be considered a special-purpose computer when so configured. In addition, some or all portions of the processes may be performed by hardware specifically configured for carrying out the processes.

The computing system 100 may be used for the video phones, servers, and computers, computing devices, processing devices, and communication devices described herein with varying levels of optional components.

Figure 2:
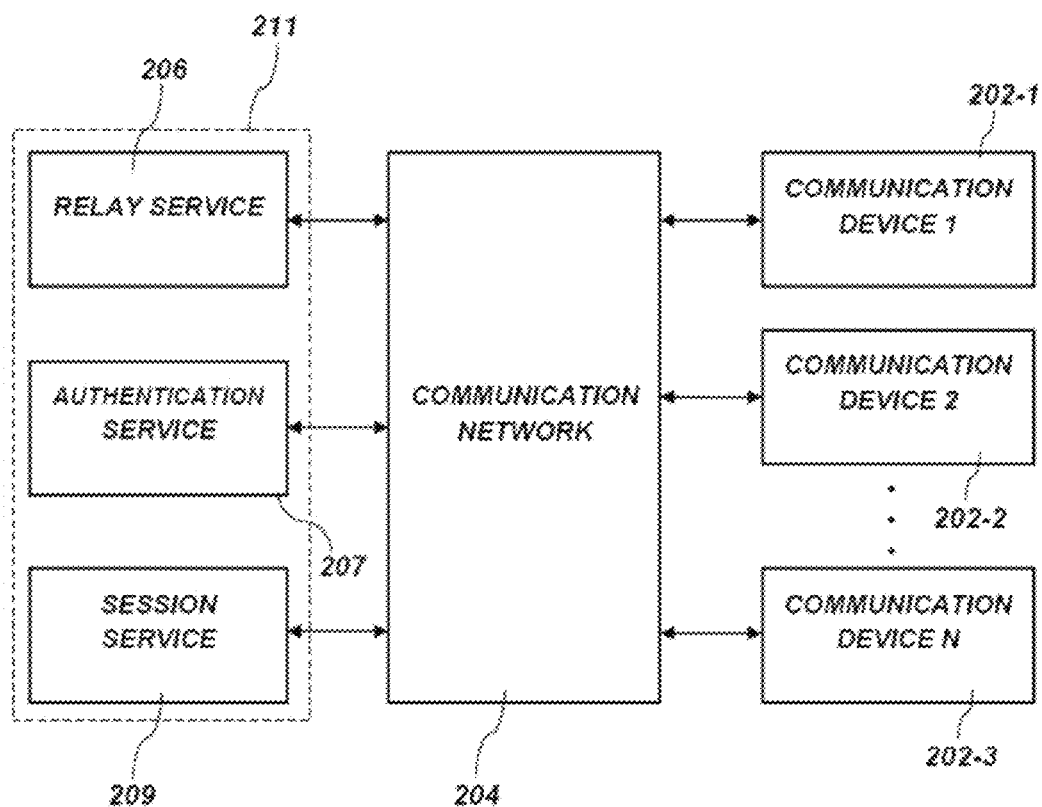
FIG. 2 is a simplified block diagram of a communication system.

FIG. 2 is a simplified block diagram of a communication system 200. The communication system 200 may include a plurality of communication devices 202. The communication system 200 may also include a communication network 204, and one or more servers 211.

Each of the plurality of communication devices 202 may comprise a communication device for the hearing impaired, including a video phone capability. Although the simplified block diagram of FIG. 2 illustrates three communication devices 202-1, 202-2, 202-3, the present disclosure contemplates any number, including one, of communication devices.

Each of the plurality of communication devices 202 may be placed in different locations in or around a building. By way of example, and not of limitation, the plurality of communication devices 202 may each be placed in a different room of a dwelling. One or more of the plurality of communication devices 202 may additionally be placed in locations remote from others of the plurality of communication devices 202, such as in different buildings. By non-limiting example, one or more communication devices 202 may be located at a user's home, and another communication device 202 may be located at the user's place of employment.

The plurality of communication devices 202 may be physical hardware devices such as, for example, video phones, telephones, and cellular telephones. The plurality of communication devices 202 may also be software endpoints configured to be accessed on devices configured to execute software commands, such as, for example, smart phones, tablet computers, desktop computers, laptop computers, and HDMI sticks.

Each of the plurality of communication devices 202 may be configured to connect to the one or more servers 211 through the communication network 204. The communication network 204 may comprise any one or combination of a personal area network (PAN), a local area network (LAN), a wide area network (WAN), or other kind of network.

The one or more servers 211 may be configured to provide services to the one or more communication devices 202. The one or more servers 211 may include a relay service 206 configured to provide a hearing impaired user the ability to communicate with standard telephone users, such as, for example, hearing capable individuals. By way of non-limiting example, the relay service 206 may include a sign language translation service, a text to voice service, a voice to text service, or combinations thereof. The relay service 206 is configured to connect to the communication network 204.

The one or more servers 211 may also include an authentication service 207 configured to authenticate the user of a communication device 202, allowing that user to control the functionality of the communication device 202 and/or access the services provided by the one or more servers 211. The authentication service 207 is configured to connect to the communication network 204.

The one or more servers 211 may additionally include a session service 209. The session service 209 may be configured to initiate and administer communication sessions for the communication devices 202. The communication sessions may include communications such as voice communications and video communications. By way of non-limiting example, the communication sessions may include the sign language translation, text to voice, and voice to text communication sessions discussed above with respect to the relay service 206. Also by way of non-limiting example, the session service 209 may utilize a Session Initiation Protocol (SIP), an H.323 protocol, and other suitable protocols.

In some embodiments, the one or more servers 211 may be a single server device connected to the communication network 204. The various functions described with respect to the relay service 206, the authentication service 207, and the session service 209 may consequently be performed by a single device. In other embodiments, the one or more servers 211 may be more than one server device. The various functions described with respect to the relay service 206, the authentication service 207, and the session service 209 may consequently be performed by separate server devices. In still other embodiments, the various functions of the relay service 206, the authentication service 207, and the session service 209 may be performed by two or more server devices, and may not necessarily be isolated to separate server devices.

A text captioned telephone system employs a relay service in a mode where the relay transmits both the voice of the hearing user and a text stream of the words spoken by the hearing user. A hearing-impaired user using a text captioned telephone, or telephone enabled to do text enhanced telephony, may carry on a normal telephone conversation with a hearing user while a text transcription of the words spoken by the hearing user is displayed on the text captioned telephone. The text transcription may allow the hearing-impaired user to confirm his or her understanding of the words spoken by the hearing user.

A video relay service enables a hearing-impaired user (may also be referred to herein as a deaf party or deaf user) to engage in conversation through the communication system with a hearing-capable user. The hearing-impaired user may exhibit varying levels of impairment and may be a voice-capable hearing-impaired user or a voice-incapable hearing-impaired user. A communication session between the users is facilitated through the use of various equipments, which are preferably coupled together using one or more networks.

To interface a hearing-impaired user into a generally voice-based communication system, interpretive services are employed allowing hearing-impaired users to communicate with a translator, such as, for example, through sign language. One means for relaying the communicative expressions of a hearing-impaired user within the communication system incorporates a video phone for capturing and displaying the communicative expressions exhibited by the hearing-impaired user and for displaying interpreted voice information originating from the hearing-capable user. The expressions, such as sign language and/or body language, may be interpreted or translated by a Video Relay Service (VRS). The hearing-capable user interacts in a conventional manner with the translator at the VRS through a voice-based dialogue conveyed over a conventional voice phone while the hearing-impaired user converses with the translator at the VRS with a video connection to support sign language. Embodiments of the present disclosure can use both video relays services as well as text captioning relay services.

Figure 3:
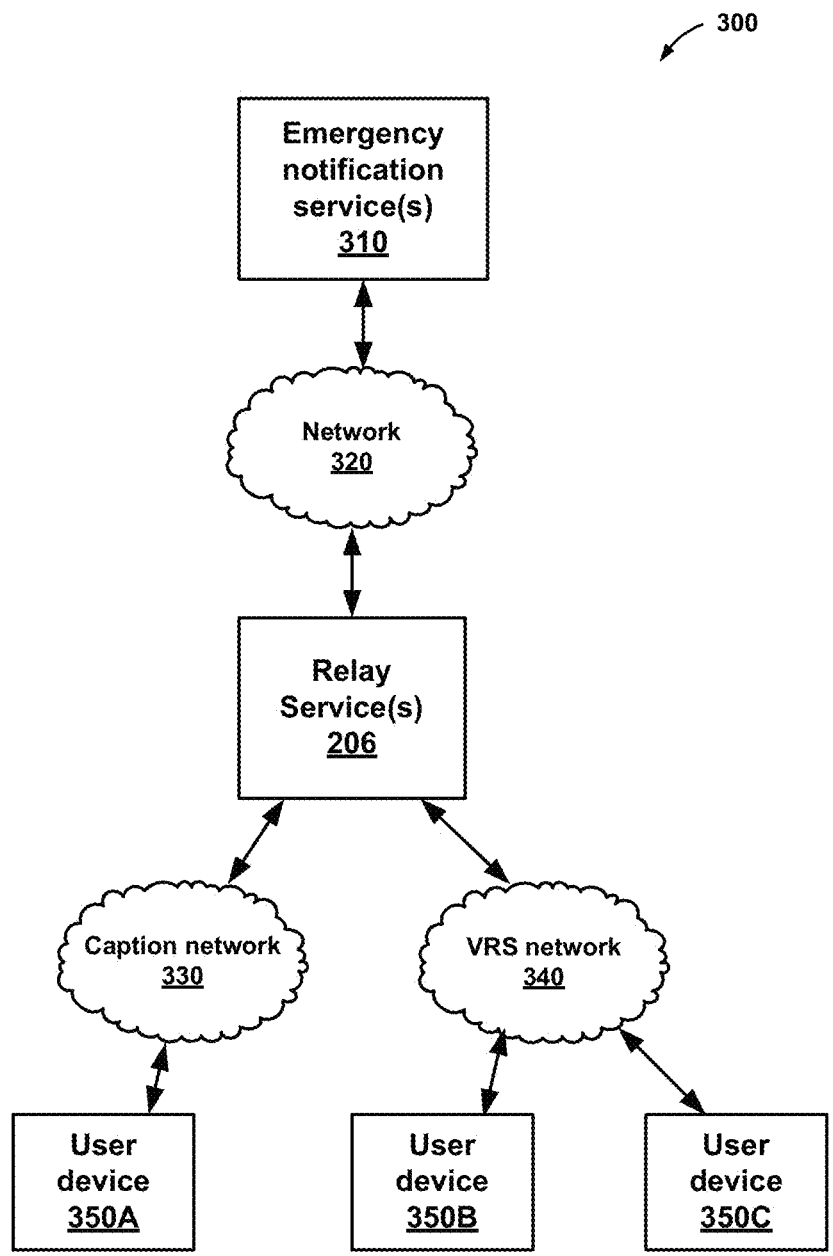
FIG. 3 is a simplified flow diagram showing movement of emergency alert information between various participants in embodiments of the present disclosure.

FIG. 3 is a simplified flow diagram showing movement of emergency alert information between various participants in embodiments of the present disclosure. Emergency notification services 310 may be many types of services that are available over the Internet. As non-limiting examples, such services include national weather service alert systems, and Integrated Public Alert and Warning System (IPAWS). A relay service 206 for the hearing-impaired may regularly query these emergency notification services 310 over a network 320, such as the Internet. The relay service 206 may then process any found emergency alerts to determine if it is appropriate to notify any of its subscribers of the found alerts. If the relay service supports text captioning relay services, the relay service 206 may send the emergency alerts to a hearing-impaired user device 350A over a caption network 330. If the relay service supports video relay services, the relay service 206 may send the emergency alerts to a hearing-impaired user device 350B, 350C over a VRS network 340. In some embodiments, network 320, caption network 330, and VRS network 340 may all be the same network and may be the Internet.

Figure 4:
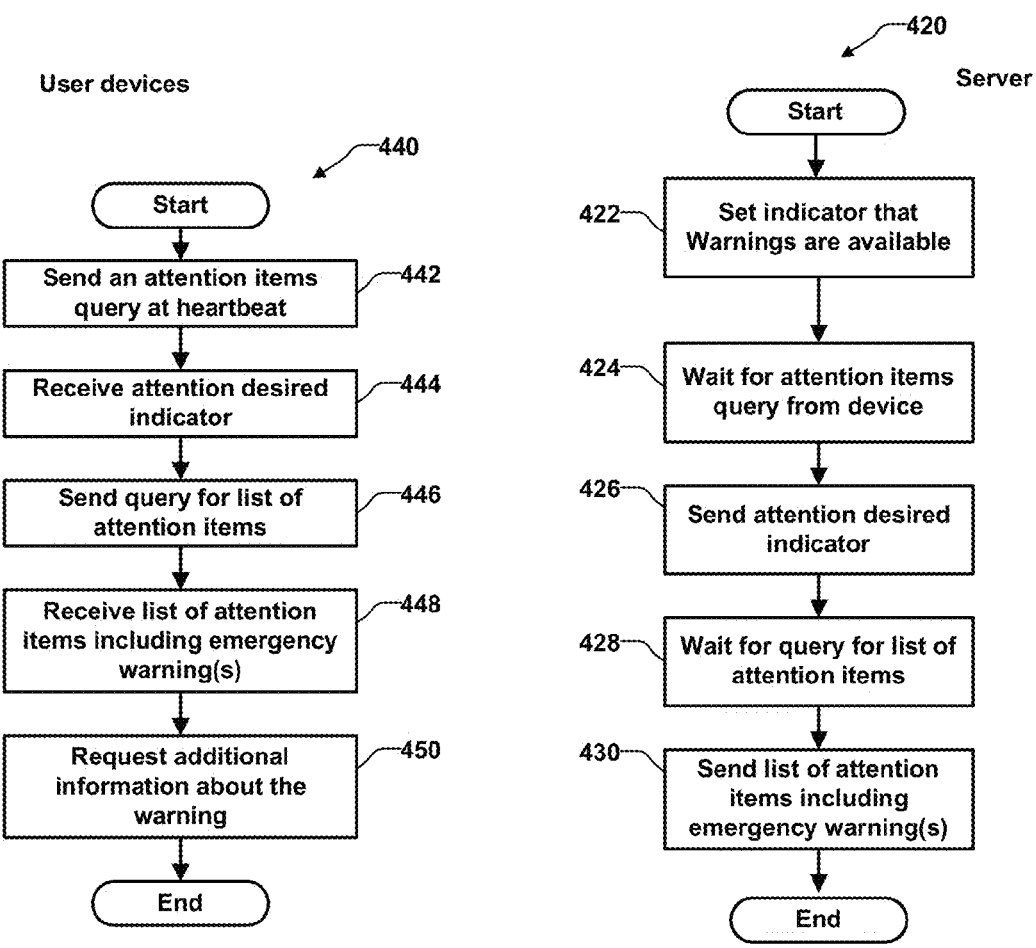
FIG. 4 is a flowchart illustrating a method for managing a emergency alert notifications to subscribers of a hearing-impaired relay service.

FIG. 4 is a flowchart illustrating a method for managing an emergency alert notifications to subscribers of a hearing-impaired relay service. In describing FIG. 4, reference is also made to FIGS. 2 and 3. A first process 420 occurs on a server 211 that is in communication with hearing-impaired user devices. As a non-limiting example the server may perform the relay service 206, the session service 209, or combinations thereof as described above. A second process 440 occurs on hearing-impaired user devices that are able to communicate with the server 211.

Embodiments of the present disclosure may operate on a process of periodic queries by the hearing-impaired user devices. This periodic query process is referred to herein as a heartbeat. Each hearing-impaired user device maintains its own heartbeat (e.g., a heartbeat every 10 seconds). When the heartbeat occurs, the hearing-impaired user device sends an attention items query to the server 211 asking if there are any items that need the attention of that particular hearing-impaired user device. The server 211 responds to the attention items query with an attention desired indicator, which can indicate that the server 211 has some items for the hearing-impaired user device to consider or there are no items to consider at this heartbeat.

When the hearing-impaired user device receives a positive attention items query, it may follow up with a query for a list of the attention items. When the server 211 receives this query, it sends the hearing-impaired user device a list of any items that the communication device may need to act upon.

At operation 422, the server 211 may determine that it has warnings or alerts available. At operation 424, the server may wait for an attention items query from a hearing-impaired user device.

At operation 442 each hearing-impaired user device sends an attention items query to the server at the time of its particular heartbeat. In response, at operation 426, the server 211 sends an attention desired indicator to the hearing-impaired user device that has sent the request. In embodiments of the present disclosure, if there are alerts that are appropriate for this particular hearing-impaired user device, the attention desired indicator would be positive. Of course, there may be many reasons other than emergency alerts for the server 211 to indicate that there are attention items for this particular hearing-impaired user device.

At operation 444, the hearing-impaired user device receives the attention desired indicator and, if positive, may respond with a query for the list of attention items at operation 446. Meanwhile, the server 211 may be in operation 428 waiting for the query for the list of attention items. Once received, at operation 430, the server 211 sends the list of attention items to the hearing-impaired user device. This list is received at the hearing-impaired user device at operation 448. The list may include an emergency alert indicating that the hearing-impaired user device should perform some action to notify the user of the alert. Of course, the list of attention items may include other items for the hearing-impaired user device to act upon.

At operation 450, the hearing-impaired user device may request additional information if the user has seen the emergency alert and decides that she would like to see information about the alert.

Figure 5:
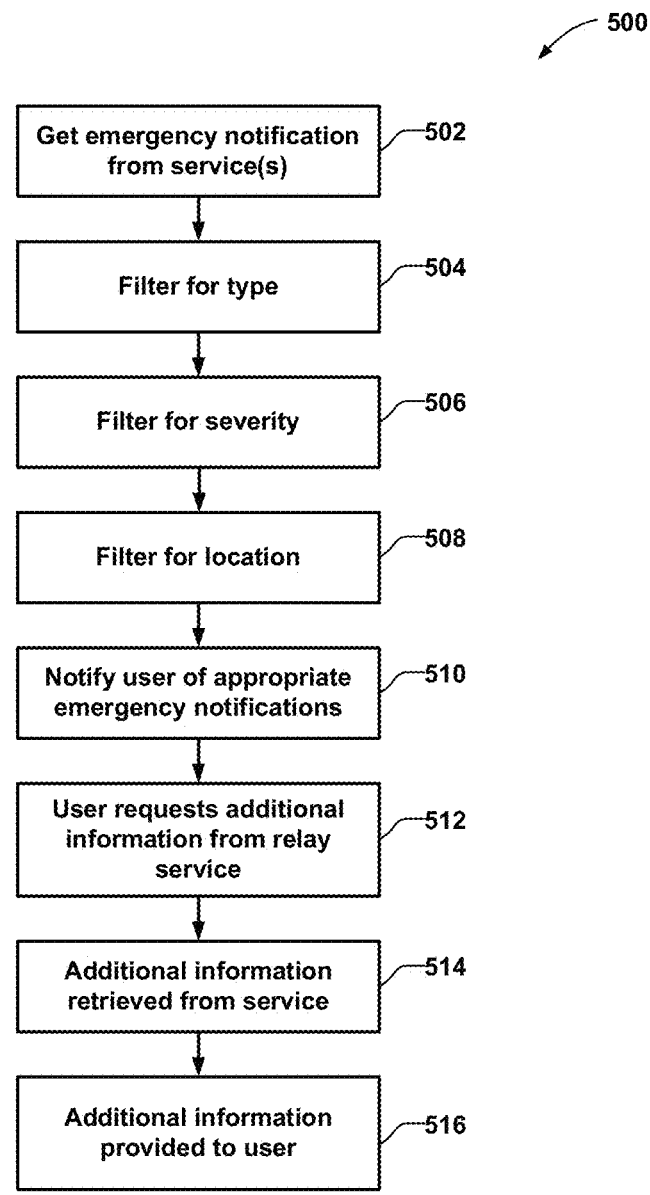
FIG. 5 is a flowchart of a process for emergency alert retrieval, processing, and delivery to hearing-impaired users.

FIG. 5 is a flowchart of a process for emergency alert retrieval, processing, and delivery to hearing-impaired users. At operation 502, the server may attempt to retrieve emergency notification from any emergency services to which it may subscribe. This may be a periodic process where the server checks every hour, minute, or even seconds between each check. At operation 504, the server may filter any alerts found based on type of alert. There may be many types of filtering parameters employed and many of them may be user selectable as discussed below. As non-limiting examples, alerts types may be alerts such as severe weather alerts, hurricane alerts, national emergency alerts, amber alerts, and traffic alerts.

At operation 506, the server may filter any alerts remaining based on severity of alert. Severity may be expanded to include criteria such as urgency, and certainty. At operation 508, the server may filter any alerts remaining based on location, as explained below. At operation 510, the server may notify the user of any appropriate emergency notifications using the heartbeat process discussed above with reference to FIG. 4. At operation 512, when the user is aware of the notification that there are alerts, the user may request additional information.

At operation 514, the server may retrieve any additional information, if needed, from the emergency notification service. At operation 516, the server may provide the additional information to the user. At this point, the server may pass on the information just like it received the information from the emergency notification service. In some embodiments, the relay service may create a video recording of the content of the emergency alert in sign language. The user can then view the video. In some embodiments, the relay service may provide links in the message so the user can find more information about the emergency alerts.

This notification process is likely to be unique for many users based on filtering setting that the user can set on the user's device.

Figure 6:
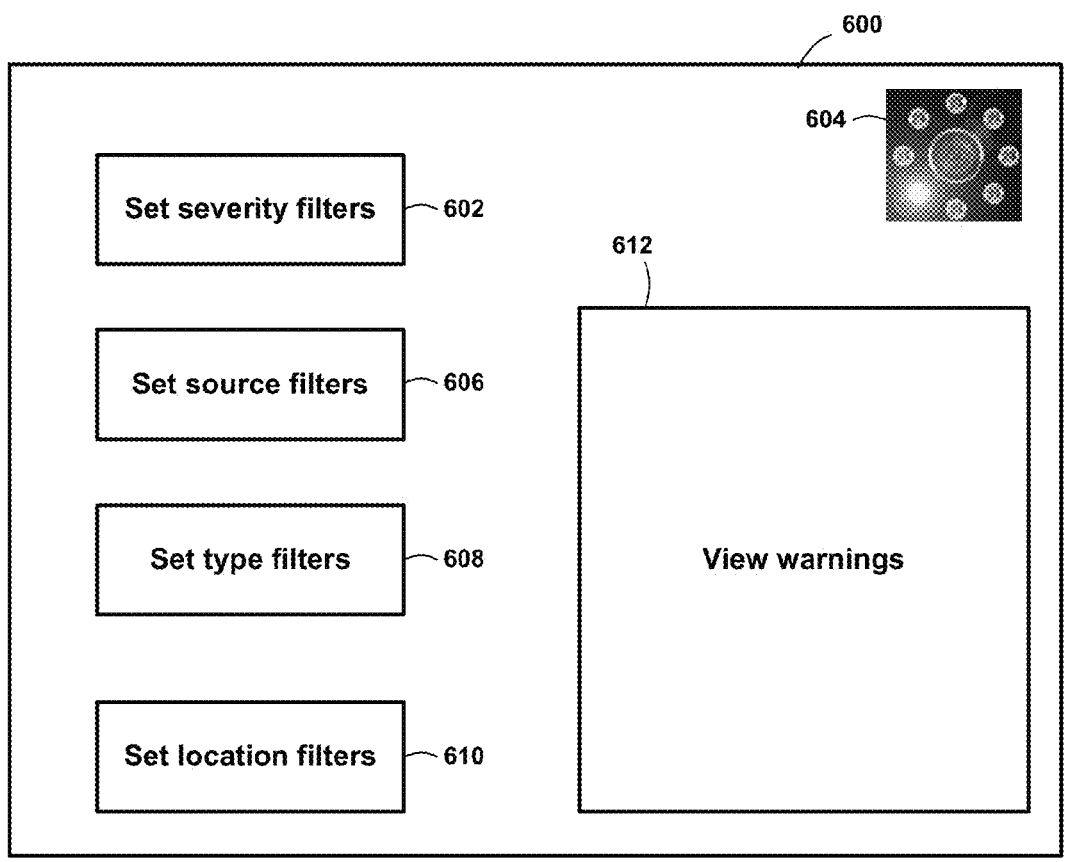
FIG. 6 is a simplified example of a Graphical User Interface (GUI) showing possible selection criteria and notification options.

FIG. 6 is a simplified example of a Graphical User Interface (GUI) 600 showing possible selection criteria and notification options. A severity filtering option 602 may be included so the user can select from different severity levels, different confidence levels, and different urgency levels. For example, a user may only want to be alerted about severe alerts that need urgent attention. A source filter 608 may be included so the user can select from where the user would like to get emergency alerts. For example, the user may only want to be notified about alerts from the national weather service or alerts from the IPAWS system.

A type filter 608 may be included such that the user is only notified about selected types of alerts. For example, the user may only want to know about flooding alerts or national security alerts.

A location filter 610 may be included so the user is only notified about alerts for a specific location. For example, the relay service may use a geocoding process for finding associated geographic coordinates (e.g., expressed as latitude and longitude) from other geographic data, such as street addresses, or ZIP codes. Many emergency notification services such as IPAWS include geolocation codes in their emergency alerts. As a result, the server could automatically filter the emergency alerts based on the geocoding process and the geolocation codes in the alerts. Alternatively, many user devices include Global Positioning Satellite (GPS) location services that could be transmitted to the server rather than using a geocoding process.

Region 612 shows a location where the warning information may be displayed. This region could include the video or links to web pages as discussed above. Alternatively, it could be the warning just as it was received by the server. Such a warning is shown in FIG. 7, which illustrates an example of an emergency alert delivered to a hearing-impaired user device.

An emergency alert notifier 604 maybe included to notify the user that there may be alerts that the user wants to get more information about. The emergency alert notifier 604 may take many forms such as a small icon on the screen, the entire screen flashing, for mobile devices, the device may vibrate, and the user device may include a physical Light Ring. As shown in FIG. 6, the emergency alert notifier 604 is an emulation of a Light Ring, which can be animated to present different light patterns. This animation may show an emulation of a lens and a light group. For example the lights may alternatively light in a circular pattern or all the lights may flash simultaneously. In addition this status indicator may be configured to emulate other LightRing configurations, such as, for example those disclosed in U.S. Pat. No. 7,769,141 to Cupal et al., the contents of which is hereby incorporated by reference in its entirety While certain illustrative embodiments have been described in connection with the figures, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of embodiments encompassed by the disclosure as contemplated by the inventors.

What is claimed is:

1. A server associated with a hearing-impaired relay service for supporting interpretive services and providing emergency alerts to hearing-impaired users, the server comprising:
    a memory configured to store computing instructions; and
    a processor operably coupled to the memory and configured to execute the computing instructions to:
        support communication sessions for hearing-impaired user devices through the hearing-impaired relay service while the hearing-impaired user devices communicate with a remote device associated with a hearing-capable user;
        receive emergency alert notifications from one or more external emergency alert services over an external network;
        filter at least some of the received emergency alert notifications responsive to user selected criteria to select one or more filtered emergency alerts;
        transmit an attention desired indicator directly to the hearing-impaired user devices that are supported by the hearing-impaired relay service if the one or more filtered emergency alerts are present that fit within the user selected criteria for the corresponding hearing-impaired user device;
        receive an emergency information query from the hearing-impaired user device that is sent responsive to the attention desired indicator;
        generate a video recording with a sign language translation of the received emergency alert notifications; and
        transmit at least one of the one or more filtered emergency alerts comprising the video recording with its corresponding sign language translation directly to the hearing-impaired user devices in response to the emergency information query from the hearing-impaired user device.

2. The server of claim 1, wherein the one or more filtered emergency alerts comprises information as it was received from the one or more emergency alert services.

3. The server of claim 1, wherein the processor is further configured to execute the computing instructions to filter the emergency alert notifications for a selected severity level or higher.

4. The server of claim 1, wherein the processor is further configured execute the computing instructions to filter the emergency alert notifications responsive to at least one of a selected source of the emergency alert and a selected type of the emergency alert.

5. The server of claim 1, wherein the processor is further configured to execute the computing instructions to filter the emergency alert notifications responsive to one or more selected locations.

6. The server of claim 5, wherein the processor is further configured to execute the computing instructions to determine at least one of the one or more selected locations from a geolocation process using a known address for the hearing-impaired user device.

7. The server of claim 5, wherein the processor is further configured to execute the computing instructions to determine at least one of the one or more selected locations from a global positioning satellite process for the hearing-impaired user device.

8. The server of claim 1, wherein the hearing-impaired relay service is a video relay service configured to provide a sign language interpretation of a voice signal from the remote device to the hearing-impaired user device during the communication session, or a text captioning relay service configured to provide text captioning of the voice signal from the remote device to the hearing-impaired user device during the communication session.

9. A method for operating a hearing-impaired relay service integrated with providing emergency alerts to a hearing-impaired user, the method comprising:
    facilitating a communication session between a hearing-impaired user device and a remote device associated with a hearing-capable user through a hearing-impaired relay service providing translation services for the communication session;
    receiving emergency alert notifications at the hearing-impaired relay service from one or more emergency alert services over an external network;
    filtering at least some of the emergency alert notifications at the hearing-impaired relay service responsive to user selected criteria to select one or more filtered emergency alerts;
    generating video data including a sign language interpretation of the one or more filtered emergency alerts;
    transmitting an attention desired indicator from the hearing-impaired relay service to the hearing-impaired user device if the one or more filtered emergency alerts are present; and
    transmitting at least one of the one or more filtered emergency alerts including the video data with its corresponding sign language interpretation from the hearing-impaired relay service to the hearing-impaired user device in response to an emergency information query being received from the hearing-impaired user device.

10. The method of claim 9, wherein the one or more filtered emergency alerts comprises information as it was received from the one or more emergency alert services.

11. The method of claim 9, wherein filtering the emergency alert notifications is responsive to the user selected criteria selected from the group consisting of one or more selected locations, a selected severity level, a selected confidence level, a selected urgency level, a source of the emergency alert notification, type of the emergency alert notification, or a combination thereof.

12. A communication device specifically configured for use by a hearing-impaired user, the communication device comprising:
    a display configured to present information to a hearing-impaired user;
    a memory configured store computing instructions; and
    a processor operably coupled to the memory and configured to execute the computing instructions to:
        establish communication sessions with a remote communication device associated with a hearing-capable user with the assistance of a relay service configured to provide translation assistance for the hearing-impaired user during a communication session;
        send an attention items query to the hearing-impaired relay service requesting to be notified if there are items related to emergency alert notifications that the hearing-impaired relay service has received from one or more external emergency alert services over an external network;
        send an emergency information query to the hearing-impaired relay service in response to receiving a notification from the hearing-impaired relay service that there are emergency alert notifications for the communication device to consider;
        receive at least one of the emergency alert notifications including a video recording of a sign language translation for the at least one emergency alter notification from the hearing-impaired relay service; and
        present information including the video recording related to the received emergency alert notifications on the display.

13. The communication device of claim 12, wherein the processor is further configured to execute the computing instructions to cause a GUI to be presented on the display, wherein the GUI enables a user to select options for filtering at least some of the emergency alert notifications.

14. The communication device of claim 12, wherein the processor is further configured to execute the computing instructions to cause the display to present an emergency alert notifier indicating at least some of the emergency alert notifications are available to be considered by the user.

15. The server of claim 1, wherein the server is a relay server configured to provide the hearing-impaired user device with the ability to communicate with standard telephone users.

16. The server of claim 1, wherein the server is a session server configured to initiate and administer the communication sessions for the hearing-impaired user devices.

17. The server of claim 1, wherein the processor is configured to further execute the computing instructions to transmit additional items for the hearing-impaired user device to act upon along with the transmission of the one or more filtered emergency alerts.

18. The communication device of claim 12, wherein the processor is configured to execute the computing instructions to send the attention items query to the hearing-impaired relay service as part of a regular heartbeat to query hearing-impaired relay service.

* * * * *

UNITED STATES PATENT AND TRADEMARK OFFICE
CERTIFICATE OF CORRECTION

| | | |
|---|---|---|
| PATENT NO. | : 9,214,094 B2 | Page 1 of 1 |
| APPLICATION NO. | : 13/838487 | |
| DATED | : December 15, 2015 | |
| INVENTOR(S) | : Steve Taggart et al. | |

It is certified that error appears in the above-identified patent and that said Letters Patent is hereby corrected as shown below:

In the claims:

| | | |
|---|---|---|
| CLAIM 4, | COLUMN 10, LINE 45, | change "configured execute" to --configured to execute-- |
| CLAIM 12, | COLUMN 11, LINE 46, | change "configured store" to --configured to store-- |

Signed and Sealed this
Seventh Day of June, 2016

Michelle K. Lee
*Director of the United States Patent and Trademark Office*